United States Patent [19]

Udeinya

[11] Patent Number: 5,370,873
[45] Date of Patent: Dec. 6, 1994

[54] THERAPEUTIC COMPOUNDS DERIVED FROM THE NEEM TREE

[76] Inventor: Iroka J. Udeinya, 422 N. Horners La., Rockville, Md. 20850

[21] Appl. No.: 944,201

[22] Filed: Sep. 11, 1992

[51] Int. Cl.$^5$ .............................................. A61K 35/78
[52] U.S. Cl. .................................. 424/195.1; 514/934; 514/896
[58] Field of Search ...................... 424/195.1; 524/934, 524/896

[56] References Cited

U.S. PATENT DOCUMENTS

| | | | |
|---|---|---|---|
| 4,515,785 | 5/1985 | Simiza et al. | 424/195.1 |
| 4,536,496 | 8/1985 | Shimiza et al. | 424/54 |
| 4,537,774 | 8/1985 | Shimiza et al. | 424/195.1 |
| 5,196,197 | 3/1993 | Talwar et al. | 424/195.1 |

OTHER PUBLICATIONS

Pettit et al., *Journal of Natural Products* 46, 379 (1983).
Fujiwara et al., *Carbohydrate Research* 141, 168 (1985).
E. Sandstrom et al. Drug 34: 372–398, 1987.
Chung Chu et al. J Med Chem 32: 612–617, 1989.

*Primary Examiner*—John W. Rollins
*Assistant Examiner*—Everett White
*Attorney, Agent, or Firm*—Venable, Baetjer, Howard & Civiletti

[57] ABSTRACT

The present invention relates to purified extracts from Neem leaves. The extracts inhibit the adhesion of infectious cells and cancer cells to endothelial cells. The extracts also inhibit viruses, and malaria parasites in both the asexual and sexual forms. The invention also relates to a method of extraction, and pharmaceutical preparations containing the purified extracts.

8 Claims, 11 Drawing Sheets

THERAPEUTIC COMPOUNDS DERIVED FROM THE NEEM TREE

FIELD OF THE INVENTION

1. Field of the Invention

The present invention broadly relates to compounds which are derived from the Neem tree. These compounds demonstrate in vitro activity against malaria, cancer and AIDS.

BACKGROUND ART

Neem (*Azadirachta Indica*) is a plant which is used in India and Africa for the treatment of the symptoms of malarial fevers and a variety of other illnesses, including skin diseases and inflammations. Usually, a crude, unpurified aqueous or alcoholic extract of the Neem leaves, bark and/or roots is utilized for this symptomatic treatment. Neem seeds and oils are also used topically to treat skin infections and as insecticides and insect repellents.

The extraction of some antitumor substances from Neem bark has been reported by Pettit et al., *Journal of Natural Products*, Vol. 46 pp. 379-390 (1983) and Fujiwara et al., *Carbohydrate Research* 141, 168 (1985). These extracts were described as being useful for their toxic effects on cancer cells. However, these substances, like many other compositions used to treat cancer, are also toxic to noncancerous cells.

Similarly, several United States patents have reported Neem bark extracts which purportedly demonstrate antimitotic activity in fertilized sea urchin eggs and growth-inhibitory action against mouse sarcoma 180 ascites and solid tumors, and mouse L-5178Y cells. These patents are U.S. Pat. Nos. 4,515,785, 4,536,496 and 4,537,774 to Shimira et al.

The Neem tree (*Azadirachta Indica*) is a medicinal plant that grows wild in many parts of the world where the climate is warm, particularly in Asia and Africa. In Nigeria it is popularly called dogonyaro. All over Africa and Asia different parts of the Neem tree, leaves, bark and seed are employed as remedies for various human ailments. Neem medicinal products are widely used for treatment of skin diseases, inflammations, rheumatic diseases and fever. They are also employed extensively as antiparasitic agents in the treatment of helminthic and protozoal infections. In India, Neem oil and its isolates nimbidiol, nimbidin and diethylsulfides are used as anti-mycobacterial and antibacterial agents. In support of the diverse medicinal applications of Neem, extracts and isolated compounds from Neem exhibit various pharmacological activities. For instance, as an anti-inflammatory agent, an aqueous extract of Neem stem bark decreases both classical and alternative complement pathway activity, reducing complement- dependent responses, anaphylaxis, chemotaxis, opsonization and stimulation of macrophages and polymorphonucleoleucocytes. It also inhibits phorbol myristate acetate-stimulated chemiluminescence. Neem leaf extracts and isolated tetranortriterpenoids, gedunin and nimbolide, have been shown by various studies to inhibit the development of the human malarial parasite *Plasmodium falciparum* in vitro. Neem compounds, 7-acetyl neotrichilenone and 1,2-diapoxyazadiradione, were reported to inhibit the murine P-388 lymphocytic leukemia cell line with $ED_{50}$ of 10 mg and 8.5 mg, respectively. Studies with various isolated Neem compounds have indicated that most of the medicinal and biological activity of the Neem is associated with the structural classes of limonoids, flavonoids, and macrolides, with sulfurated compounds playing minor roles.

Despite the extensive and centuries of use of Neem medicines, reports of toxicity in humans remain scanty. Experiments in mice suggest that various Neem compounds particularly oils, in large doses may produce toxicity. On the other hand, experiments in rats and dogs with nimbidin (a Neem compound) failed to demonstrate any systemic toxicity. Human subjects given Neem oil, 7 grams per person, orally, or 1 gram by intramuscular injection experienced no local or systemic side effects. Thus there is the expectation of low toxicity in its use as a drug and in handling the material. Interestingly, compounds isolated from the Neem leaves are azadiractin and related compounds which are very potent insect feeding repellents. This is a mechanism for the successful survival of this tree.

SUMMARY OF THE INVENTION

The present invention relates to a purified extract of Neem leaves which inhibits the adhesion of cancer cells and malarial-infected erythrocytes to cultured endothelial cells. The purified extract also inhibits the in vitro vital development of human immunodeficiency virus (HIV) in vitro, yellow fever virus and sandfly fever (Sicilian) virus, and inhibits in vitro development of both sexual (gametocytes) and asexual (schizonts) forms of human malarial parasites.

The present invention also relates to a process for extracting the purified extract from crude Neem leaves by soxhlet extraction followed by passive precipitation and high pressure liquid chromatography (HPLC) fractionation.

Another aspect of the invention is pharmaceutical compositions prepared from the purified extract.

BRIEF DESCRIPTION OF THE DRAWINGS

The various objects, advantages and novel features of the invention will be more readily appreciated from the following description when read in conjunction with the appended figures, in which.

DETAILED DESCRIPTION OF THE INVENTION

Extraction and Purification Process

Neem leaves are the starting point in the process for extraction of a useful substance, and are readily available from a variety of sources including Enugu in S. E. Nigeria. For best results, fresh green leaves are collected from mature Neem trees, and oven-dried at about 30°–70° C., preferably 40°–50° C., over several days until they are dry and crisp (i.e., crumble upon touch). The dried leaves are then ground to a coarse powder using a blender. The coarse powder can be used immediately or stored in polytene bags at room temperature until needed.

In order to extract active compounds, the coarse powder is subjected to a soxhlet process in which about 10 to about 20 grams, preferably about 15 to about 20 grams, of coarse powder is weighed and loaded into a cellulose thimble, preferably a 33 mm × 80 mm Whatman cellulose thimble. After loading, the thimble is inserted into the soxhlet apparatus and an appropriate solvent is poured into the thimble to soak the coarse powder overnight. The soxhlet apparatus used in this process consists of a glass flask reservoir to which is connected a thimble housing which in turn is connected to a condenser, cooled by circulating cold tap water. The following day, the soaked powder is subjected to standard soxhlet extraction using the same solvent at an extraction temperature of about 70° C. to about 95° C., preferably about 70° C. to about 80° C. The extraction continues for about 24 hours or until the color of the eluate (solution flowing into the reservoir flask from the thimble) becomes colorless from its initial or starting green color. The extraction process yields a deep green cloudy liquid (extract) which is stored in sealed glass jars overnight in a refrigerator at about 0° C. to about 10° C., or at room temperature.

A variety of well known solvents can be used in the extraction process including polar organic solvents such as alcohols, acetone, and pyridine and water, and mixtures thereof. However, a preferred solvent is a 50/50 mixture of acetone and distilled water. When about 15 to 20 grams of coarse Neem leaf powder is used, then about 25 to about 50 ml of the solvent is used for soaking, and about 100 ml of solvent is used for the extraction.

The process for recovery of extracted compounds from the liquid extract takes place in a standard rotor-evaporation system. The rotor evaporation system is an all glass apparatus consisting of glass rotor flask, which contains the extract, connected by a connecting column to a water cooled condenser. The base of the condenser is connected to a solvent collection flask. The entire apparatus is connected via the condenser to a variable vacuum source. This system is used to recover both the solvent and the extracted compounds from the liquid extract, using standard procedures under vacuum at about 60° C. to about 90° C., preferably about 80° C. to about 90° C. In this case, the procedure consists of heating the extract under reduced pressure using a water bath at 60°–90° C. to evaporate the extraction solvent with the extract-containing rotor flask being rotated continuously.

During the rotor-evaporation process, fractions of the extracted compound continuously separate and precipitate on the sides of the rotor flask. As evaporation continues and after all the solvent is expelled, a brown oily liquid-residue remains at the bottom of the rotor flask. This oily liquid is poured into a drying pan and dried to a paste overnight in air at about 30° C. to about 60° C., preferably about 30° C. to about 40° C. The dried residue is recovered and is designated IRC.

To recover the precipitates on the sides of the rotor flask, about 20 to 50 ml, preferably about 20 to about 30 ml of an appropriate solvent (preferably acetone) is poured into the flask to dissolve the precipitate. The solution is then poured into a glass beaker and the solvent evaporated at room temperature over one to two days. The residue left after the evaporation of the solent is recovered and designated IRAB.

The IRAB extraction product is used to prepare a stock solution containing 100 mg of IRAB per ml of solution. The stock solution is prepared by dissolving the IRAB in an appropriate solvent such as water, methanol, acetonitrile or preferably dimethyl sulfoxide (DMSO) at about 37° C. For analysis, this stock solution is diluted to a desired concentration (between about 10 and about 50 mg/ml) before fractionation by analytical high pressure liquid chromatography (HPLC).

The HPLC fractionation is preferably conducted in prepacked 300 mm × 7.8 mm I.D. 10 $\mu M$ $\mu$ Bondapak $C_{18}$ preparative column (Waters Assoc.). The stationary phase of $\mu$ Bondak $C_{18}$ is an octadecylsilyl bonded-phase packing material. The solid support medium contained in the column is capable of operating within a pH range of 2 to 8 and is thermally stable over a wide temperature range (<300° C.). due to its excellent hydrolytic stability, various hydrophilic-hydrophobic mixed solvent systems are compatible with the column, such as acetonitrile/acetic acid.

The mobile phase preferably consists of 0.02M glacial acetic acid mixed with acetonitriles, and two high pressure pumps are used to deliver the mobile phase. The acetonitrile/0.02M acetic acid at a 35:65 percent ratio is used in an isocratic mode. The flow-rate is preferably about 1.5 ml/minute, and the column pressures range between about 72 and about 80 bar. All the separations are performed at ambient temperatures and sample volumes are introduced into the column through a continuous flow loop injector. Fractionated aliquots containing the chromatographed peaks are collected during multiple injections of the crude extracts, and detection of each peak is accomplished using an ultraviolet detector, set at 254 nm. The peak areas are then preferably measured by an on-line computing integrator.

Under the above fractionation conditions, compounds designated IRDNA and IRDNB appeared as separate chromatographic peaks eluting at variable retention times (RT) of 25–28 minutes for IRDNA and 29–31 minutes for IRDNB. The amount of IRDNA and IRDNB eluted also varies in a typical fractionation. For example, when 4 mg of IRAB is fractionated, 0.6 mg and 0.9 mg of IRDNA and IRDNB, respectively are obtained representing about 15 to about 23%, respectively of the fractionated amount of IRAB.

Purified Products

As stated above, the resultant products of the extraction and purification processes described above have been designated IRAB, IRC, IRDNA and IRDNB.

Figure 1:
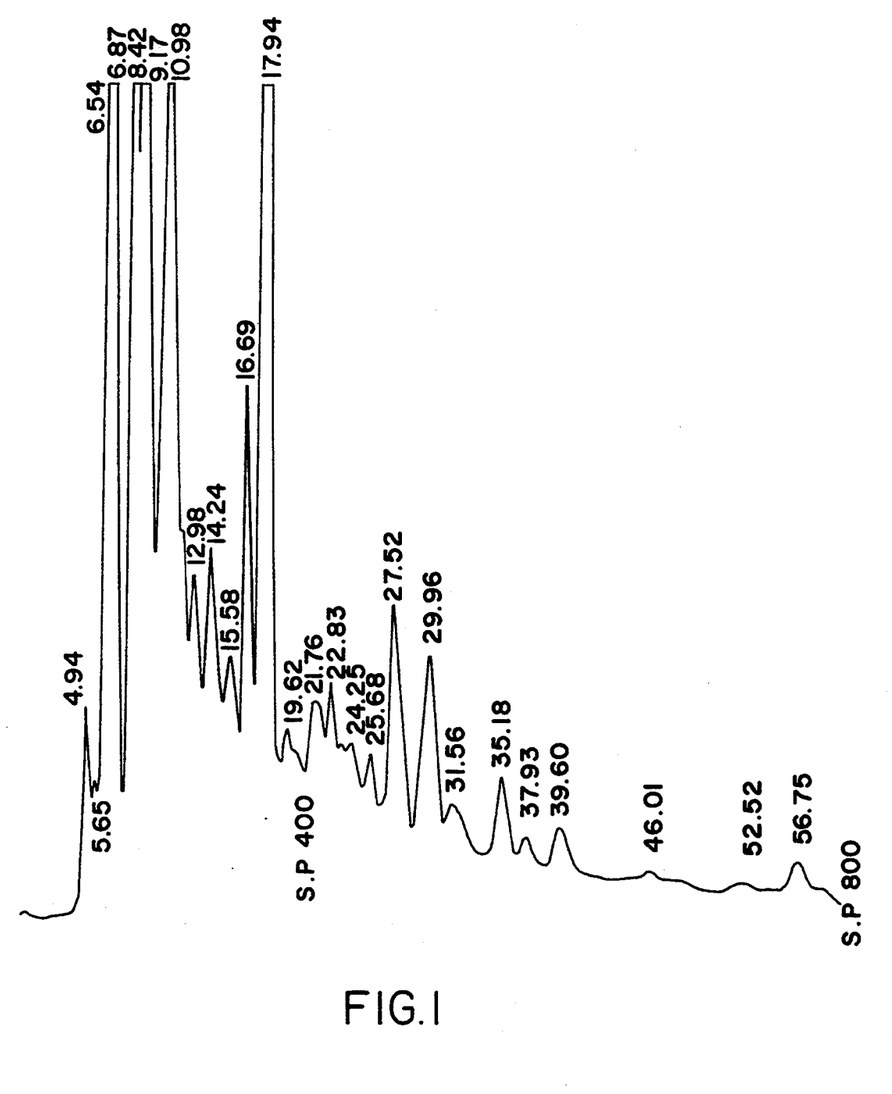
FIG. 1 shows an HPLC spectrum of an evaporation aided precipitation fraction of a Neem leaf extract desginated IRAB.

The extraction product designated IRAB is the residue after solvent evaporation of the precipitates from the sides of the rotor flask. This product is a dark green-brown pasty solid which has a strong characteristic odor, and is readily soluble in DMSO and partially soluble in water and methanol. The IRAB product is also stable at room temperature or under refrigeration, and has maintained its activity after nine years of storage at 0° C. to 20° C. The product is also stable under autoclave at 120° C. for about 15 to 25 minutes. As shown in FIG. 1, an analytical HPLC spectrum of IRAB consists of 26 distinct and separated peaks between RT 4.94 and 56 minutes with wide differences in size among the peaks.

The area of the peaks is shown in Table 1.

TABLE 1

Analytical HPLC Spectrum of IRAB

| Peak No. | Retention Time | Area | Pico-Mole | BC |
| --- | --- | --- | --- | --- |
| 1 | 4.94 | 671238 | 0.671 | BV |
| 2 | 5.65 | 8055 | 0.008 | TBB |
| 3 | 6.54 | 1899813 | 1.899 | VV |
| 4 | 6.81 | 4174217 | 4.174 | VV |
| 5 | 8.42 | 4934867 | 4.934 | VV |
| 6 | 9.17 | 6033163 | 6.033 | VV |
| 7 | 10.98 | 5902141 | 5.902 | VV |
| 8 | 12.90 | 1061507 | 0.000 | VV |
| 9 | 14.24 | 1383965 | 1.383 | VV |
| 10 | 15.58 | 745943 | 0.745 | VV |
| 11 | 16.69 | 1326996 | 1.326 | VV |
| 12 | 17.94 | 8209615 | 0.209 | VV |
| 13 | 19.62 | 630397 | 0.630 | VV |
| 14 | 21.76 | 699420 | 0.699 | VV |
| 15 | 22.83 | 633686 | 0.633 | VV |
| 16 | 24.25 | 290802 | 0.290 | VV |
| 17 | 25.68 | 171563 | 0.171 | VB |
| 18 | 27.52 | 737644 | 0.737 | BB |
| 19 | 29.96 | 903912 | 0.903 | BV |
| 20 | 31.56 | 161892 | 0.161 | TBB |
| 21 | 35.18 | 351833 | 0.321 | BB |
| 22 | 37.03 | 72870 | 0.072 | BB |
| 23 | 39.60 | 127977 | 0.127 | BB |
| 24 | 46.01 | 76028 | 0.076 | BB |
| 25 | 52.52 | 52226 | 0.052 | BB |
| 26 | 56.75 | 250956 | 0.250 | BB |

Figure 2:
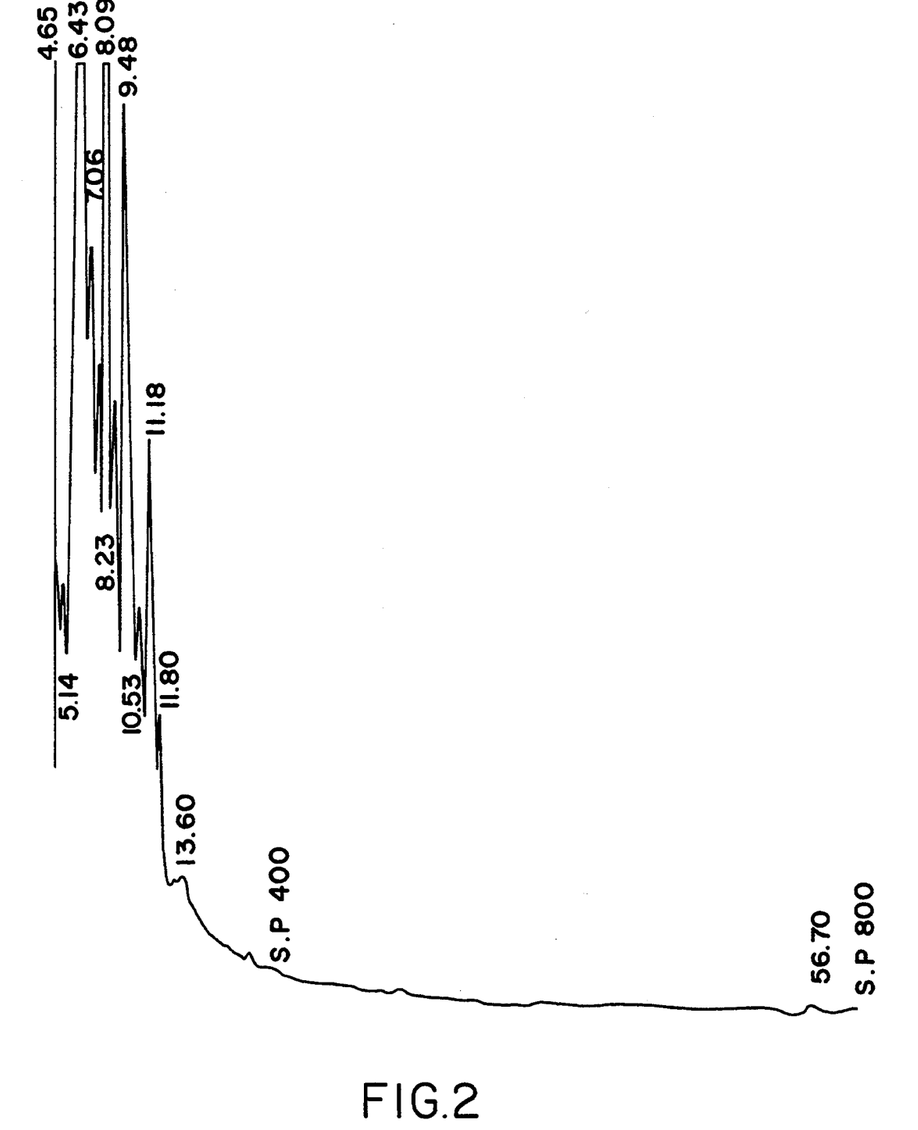
FIG. 2 shows an HPLC spectrum of a Neem leaf extract designated IRC.

The extraction product designated IRC is the dried residue of the oily liquid remaining after extraction in the rotor flask. This product is a brown semi-solid oil which has a characteristic odor, and is readily soluble in DMSO. The IRC product is also partly soluble in water and methanol where it separates into two (2) phases. The top phase is a completely dissolved brown solution, and the bottom phase consists of dirty yellowish droplets or a suspension. This product is stable for over five (5) years at 0°-20° C. As shown in FIG. 2, an analytical HPLC spectrum of IRC consists of 14 distinct and separated peaks occurring between RT 4.80 and 32.54 minutes. These peaks vary widely in size.

The area of the peaks is shown in Table 2.

TABLE 2

Analytical HPLC Spectrum of IRC

| Peak No. | Retention Time | Area | Pico-Mole | BC |
| --- | --- | --- | --- | --- |
| 1 | 4.80 | 1396561 | 1.396 | BV |
| 2 | 5.14 | 31965 | 0.031 | TBB |
| 3 | 6.46 | 4945668 | 4.945 | VV |
| 4 | 7.14 | 3618008 | 3.618 | VV |
| 5 | 7.64 | 1629474 | 1.629 | VV |
| 6 | 8.06 | 10542648 | 10.542 | VV |
| 7 | 8.56 | 2739387 | 2.739 | VV |
| 8 | 9.05 | 6750608 | 6.750 | VV |
| 9 | 10.20 | 1472578 | 1.472 | VV |
| 10 | 10.80 | 1294722 | 1.294 | VV |
| 11 | 11.38 | 1283829 | 1.283 | VV |
| 12 | 12.10 | 2534824 | 2.534 | VB |
| 13 | 24.07 | 32333 | 0.032 | BB |
| 14 | 32.54 | 27213 | 0.027 | BB |

The purified extraction product designated IRDNA is one of the HPLC fractionation products of IRAB. This product is a light brown-yellow fluffy powder which is usually carried by air after vacuum drying. This product is soluble in DMSO, and when dissolved therein retains activity for over six months. The IRDNA product is also stable and active after autoclaving at 120° C. for 10 to 25 minutes. As shown in FIG. 1, IRDNA appears in the spectrum of IRAB as a sharp, distinct peak with variable retention times. For example, in three separate HPLC analysis of IRAB, IRDNA appeared at various retention times of 25.68, 27.52, and 31.60 minutes, respectively. Variation in retention times can be caused by various factors associated with the fractionation process including variation in sample size applied to the column, speed and pressure of the fractionation, and ambient temperature.

The purified extraction product designated IRDNB is one of the products obtained following HPLC fractionation of IRAB. This product is a yellowish brown fluffy powder after vacuum drying. This product is soluble in DMSO, and stab].e therein for over six months. The IRDNB product is also stable and active after autoclaving at 120° C. for 10 to 25 minutes. As shown in FIG. 1, IRDNB appears in the spectrum of IRAB as a sharp distinct peak at various retention times. For example, in three separate HPLC profiles of IRAB, IRDNB appeared at different retention times of 27.89, 29.96, and 34.58 minutes, respectively. As stated previously, slight variations in retention times can be caused by various factors associated with the fractionation process including variation in sample size applied to the column, speed and pressure of the fractionation, and ambient temperature.

One of the important therapeutic properties of the extracted and the purified Neem leaf products is an anti-adhesive effect on cells. This property prevents traveling or metastasizing cancer cells and infectious organisms from adhering to normal cells of the body. Thus, the establishment of new colonies of cancer or infectious cells is prevented.

Anti-adhesion compounds have potential applications in many areas. The initiation of diseases, such as atherosclerosis and arthritis, is the adhesion of blood components which results in damage to the endothelium. Compounds, which prevent the adhesion of blood components, could prove useful in preventing the initiation of these disease conditions. Also, the most important initial steps in hematogenous tumor metastasis are adhesion of the circulating malignant cells to the vascular endothelium and subsequent extravasation out of the blood vessel. Therefore, compounds which could inhibit or reverse adhesion of the malignant cells could play a significant role in cancer therapy. Adhesion prevention is currently being investigated as a therapeutic mode in bacterial, vital and cancer diseases.

The result of the inability of the cancer or infectious cells to colonize due to the anti-adhesive effect of the Neem extract product is that the cancer and infectious cells are rendered ineffective and impotent. Therefore, these non-colonized cells can be eliminated from the body by natural defense mechanisms such as by the immune system.

A preferred assay for determining the presence of this anti-adhesive effect of the Neem leaf extract involves a quantification of the inhibition of the adhesion of the infectious cell to cultured endothelial cells. The infectious cell may be any disease cell such as cancer cells including monocytes, histiocytes, lymphoblastic leukemia cells, and malarial cells including *Plasmodium falciparum*, *P. berghia*, and *P. malarie* infected erythrocytes.

The infectious cells for the assay may be obtained from The American Type Culture Collection in Rockville, Md. The endothelial cells can be any cultured human endothelial cells, such as human umbilical vein endothelial cells and human microvascular endothelial cells. The preferred endothelial cells are cultured human umbilical vein endothelial cells, and may be obtained from discarded placental tissue from the labor and delivery department of any hospital.

The infected erythrocytes are treated with 0.1–10 $\mu$g/ml of IRAB, IRC, IRDNA or IRDNB for 15–30 minutes at 37° C. to permit any anti-adhesive effect that may be present to establish itself. The cultured endothelial cells are then inoculated with 1 ml of the treated infected cells, at 2% hematocrit and 2–10% parasitemia and the cultures are allowed to grow for 60–90 minutes at 37° C. Other control endothelial cell cultures are inoculated with untreated infected cells under the same conditions. A decreased level of adhesion to endothelial cells of the treated infected cells as compared to the untreated infected cell cultures indicates an anti-adhesive effect of the tested Neem leaf extract. Only IRAB had a measurable effect on adhesion. However, there has not been enough recovery of IRDNA and IRDNB (fractions of IRAB) to test their anti-adhesive properties. Since they are fractions of IRAB, it is reasonable to predict that they will exhibit the same anti-adhesive properties.

This anti-adhesive effect makes the Neem leaf extract products useful in a variety of diseases characterized by adhesive or metastasizing infectious cells including malaria, vital infections and human cancers such as human histiocytic lymphoma and lymphoblastic leukemia. However, the anti-adhesive effect of the purified Neem leaf extracts has been most useful in relation to malarial cells, and cancer cells, particularly in the case of cerebral malaria, which is characterized by adhesive obstruction of the cerebral blood vessels by malaria-infected erythrocytes.

Malarial Infection

Malaria is a unique disease characterized by a particular infectious cycle. In this cycle a parasite-bearing mosquito infects a person during a bite. The parasite, (sporozoite) enters into, and multiplies in liver cells into several thousands, and transforms into the form called merozoites. Eventually, the parasites break the liver cell and the merozoites are poured into the liver where they quickly enter red blood cells and are carried in the blood stream to all parts of the body. Once inside the blood cells, the parasites again undergo multiplication producing several daughter cells within the infected red blood cells. As the parasites mature, the red blood cells bearing the late stages of the parasite (trophozoites and schizonts) adhere to capillary and venular endothelium and are sequestered. When the parasites become fully mature, the sequestered infected cells break and are destroyed and the parasites (merozoites) are once again released. The released merozoites re-enter fresh red blood cells, thus continuing a cycle of erythrocyte invasion and destruction. When merozoites enter fresh red blood cells, some of the cells instead of continuing on the red cell destruction path, become male or female gametocytes. These forms are eventually taken up by a mosquito, where the male and female gametocytes unite and transform into sporozoites inside the mosquito. The sporozoite—bearing mosquito is then ready to start another infection the next time it bites another person—thus completing the life cycle of the human malarial parasite.

Figure 3:
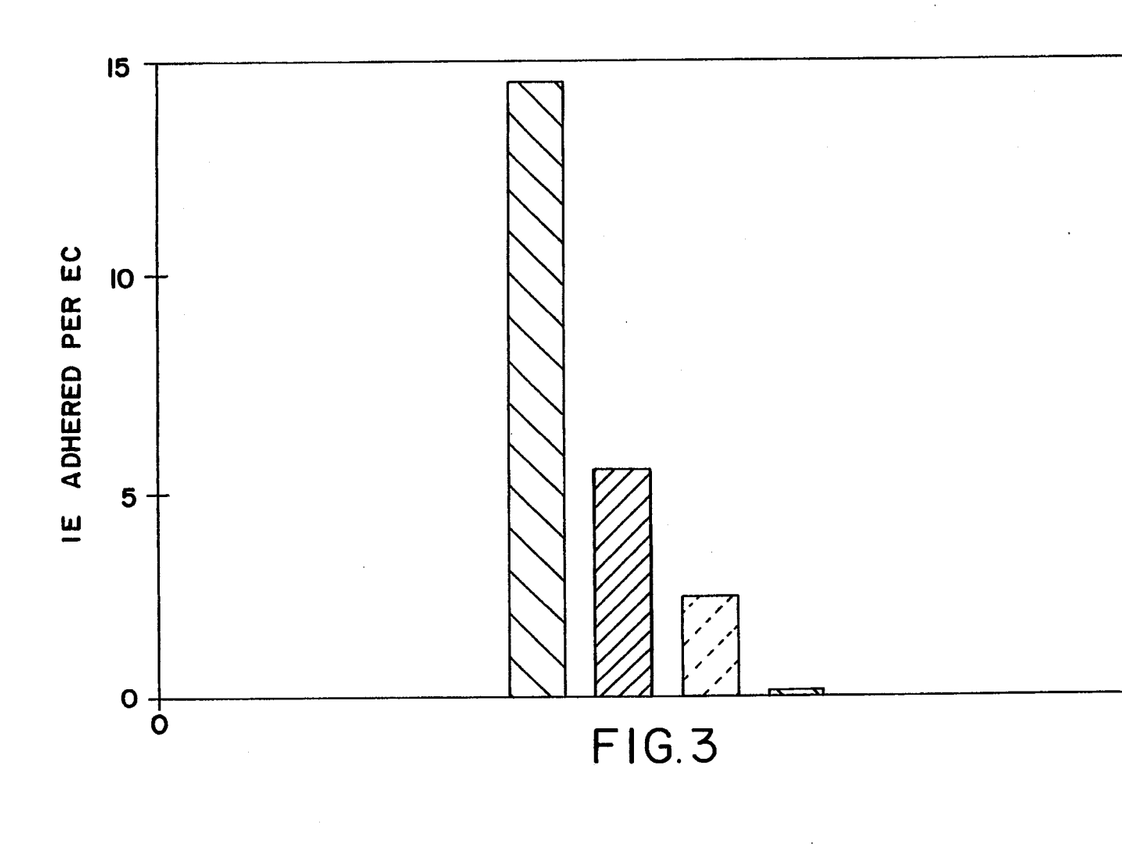
FIG. 3 graphically depicts the anti-adhesive effects of IRAB on *Plasmodium falciparum*—infected erythrocytes.

As explained above, the Neem leaf extract products are effective against malarial infection due to their anti-adhesive properties, thus preventing malaria-infected erythrocytes from sequestering. This effect is shown in FIG. 3. The bar on the far left represents the control. The next bar to the right represents IRAB pretreated infected erythrocytes (IE). The third bar represents IRAB pretreated endothelial cells (EC). The bar on the far right represents IRAB pretreated infected erythrocytes and endothelial cells. IRAB at a concentration of 5 $\mu$g/ml completely inhibited adhesion of *P. falciparum*-infected erythrocytes to human umbilical vein endothelial cells. This assay was conducted as follows. Infected erythrocytes and human umbilical vein endothelial cells were separately cultured at 37° C. in a culture chamber filled with a gas mixture comprising oxygen 5%, carbon dioxide 5%, and nitrogen 90%. After 1–2 days of culture, some of the infected erythrocytes were treated with IRAB at concentration of 5 $\mu$g/ml for 15–30 minutes. Following the treatment, 1 ml of the treated infected erythrocytes at 2% hematocrit and 5% parasitemia was added to some of the endothelial cell cultures. Untreated infected erythrocytes were added to other endothelial cell cultures as control. The cells were then allowed to incubate together for 60–90 minutes. After the incubation, nonadherent, infected erythrocytes were removed. The number of the erythrocytes adhered to the endothelial cells were determined by light microscopy. A decreased level of adhesion to endothelial cells by treated infected cells as compared to the control was considered an indication of the anti-adhesive effect of the Neem extract.

Although only IRAB was found to have a measurable anti-adhesive effect on malaria-infected erythrocytes, it has also been found that the purified extract products IRDNA and IRDNB exhibit anti-parasitic and anti-gametocyte properties in the malarial cycle. The gametocyte is the sexual stage of the malarial infection cycle which when transformed to sporozoite in the mosquito is carried by the mosquito from one infected individual to another. IRDNA and IRDNB both prevented the development of gametocytes to mature forms. In both the developing (maturing) and developed (mature) forms, of the gametocytes IRDNA and IRDNB cause disintegration of the cells. This inhibitory effect of IRDNA and IRDNB on gametocytes (gametocidal activity) has been demonstrated in vitro against the human malarial *Plasmodium falciparum* isolate NF54; while the antimalarial (i.e. schizontocidal activity) has been demonstrated in vitro against chloroquine sensitive ITG2F6 and resistant W2 strains of the *P. falcipium* malarial parasite. For assay of both the gametocidal and schizontocidal activity of the Neem extract IRAB and the purified fractions IRDNA and IRDNB, malaria-infected erythrocytes were cultured in plastic culture plates at 37° C. in an incubator containing gas mixtures as described previously. To conduct a test, the extract or the purified fractions at various concentrations, ranging from $1 \times 10^{-4}$ nanograms/ml to 5 micrograms/ml, was added to some of the cultures. Other cultures, remained as controls and did not have extracts added to them. Both the control and test cultures were then incubated for 24–72 hours. At the end of the incubation, blood smears were made and examined microscopically for parasite development. Decrease in number of parasites (schizonts or gametocytes) in the treated cultures compared to the controls was used to indicate schizontocidal or gametocidal effect.

Figure 4A:
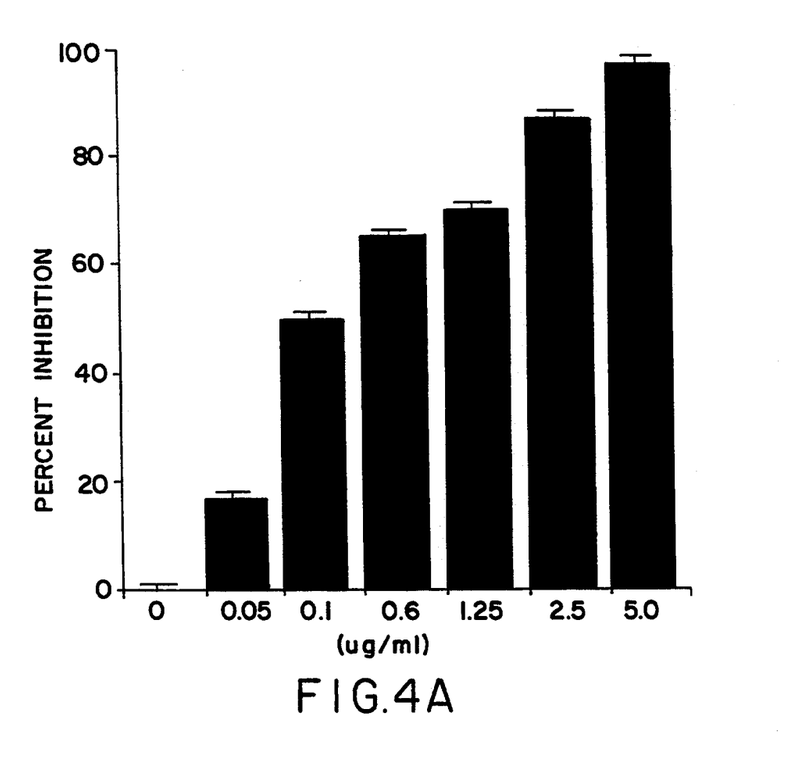
FIG. 4 shows the effect of IRAB on the development of the malarial parasite in vitro as percent inhibition and number of parasite-infected cells per 100 erythrocytes.
Figure 4B:
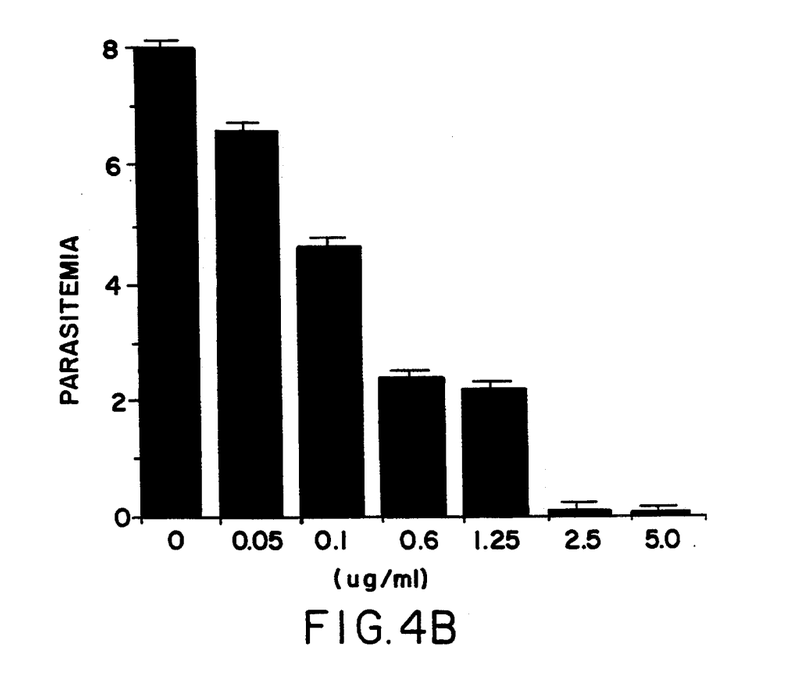
Figure 5A:
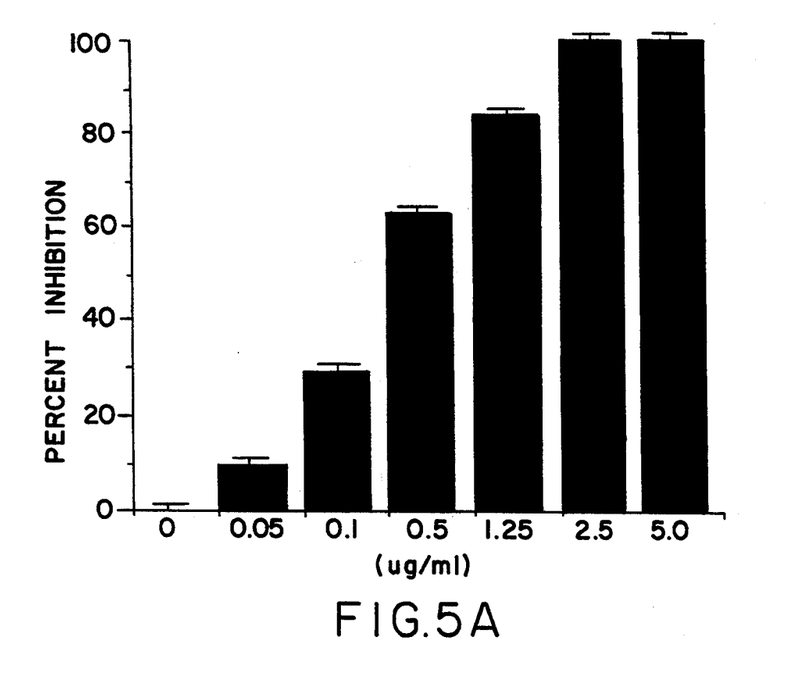
FIG. 5 shows the effect of IRAB on maturation of gametocytes in vitro as percent inhibition and number of gametocyte-infected cells per 1000 erthrocytes.
Figure 5B:
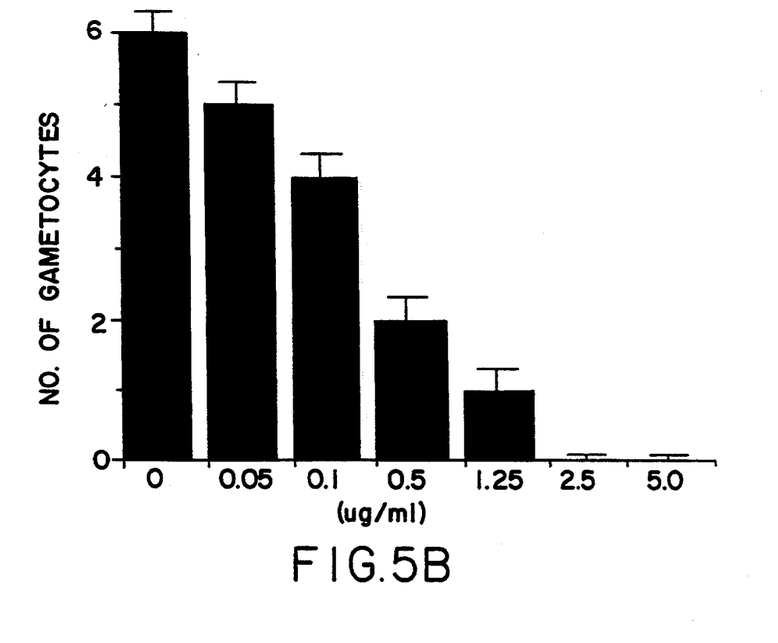
Figure 6A:
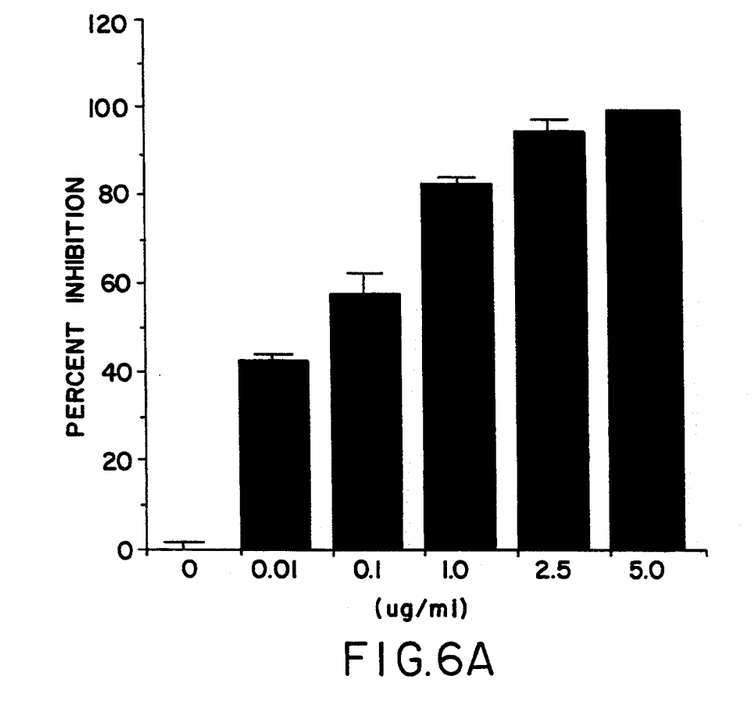
FIG. 6 shows the effect of IRAB on mature gametocytes in vitro as percent inhibition and number of gametocyte-infected cells per 1000 erythrocytes.
Figure 6B:
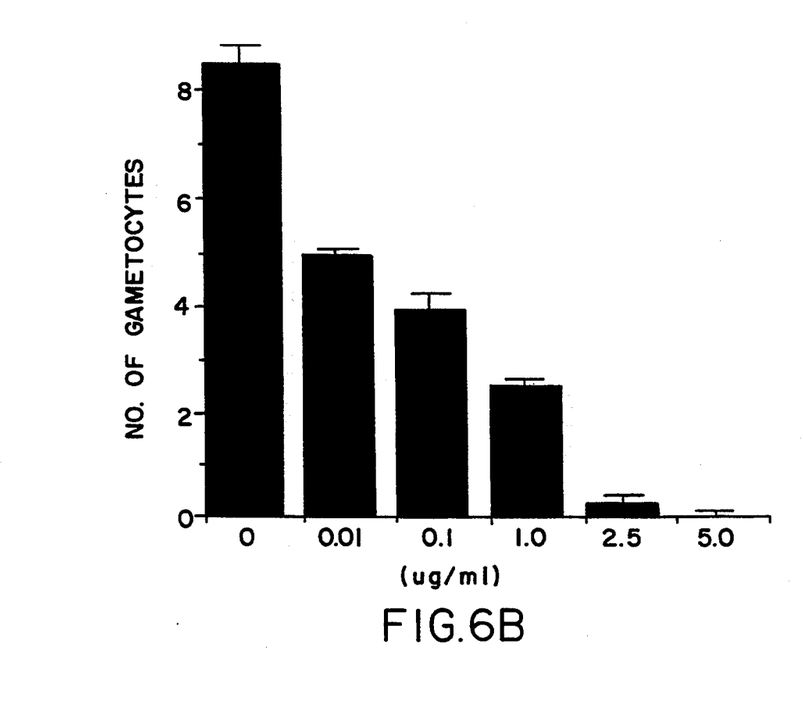
Figure 7:
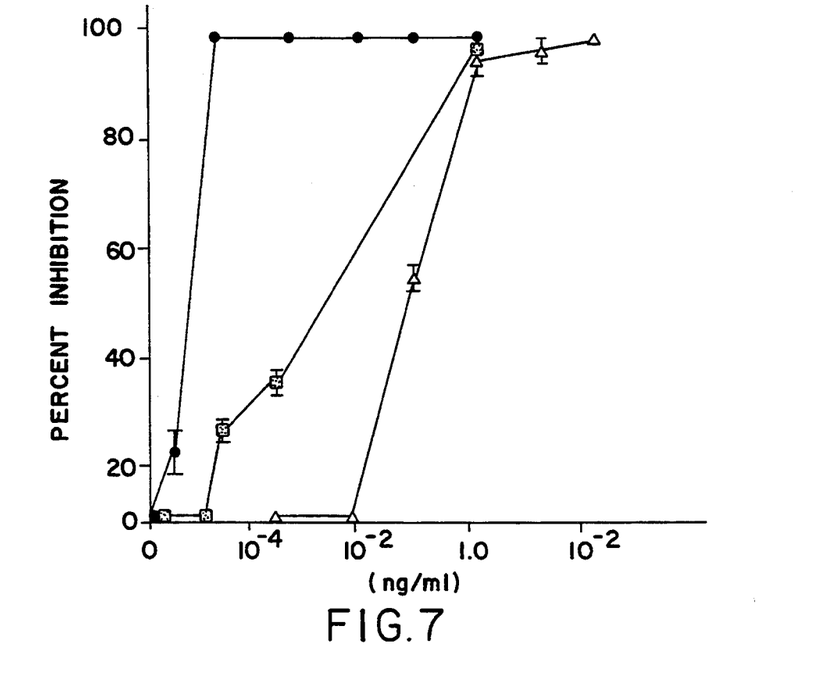
FIG. 7 graphically depicts the superior results of Neem extracts IRDNA and IRDNB as compared to chloroquine in the elimination of sexual and asexual malarial parasites in vitro.
Figure 8:
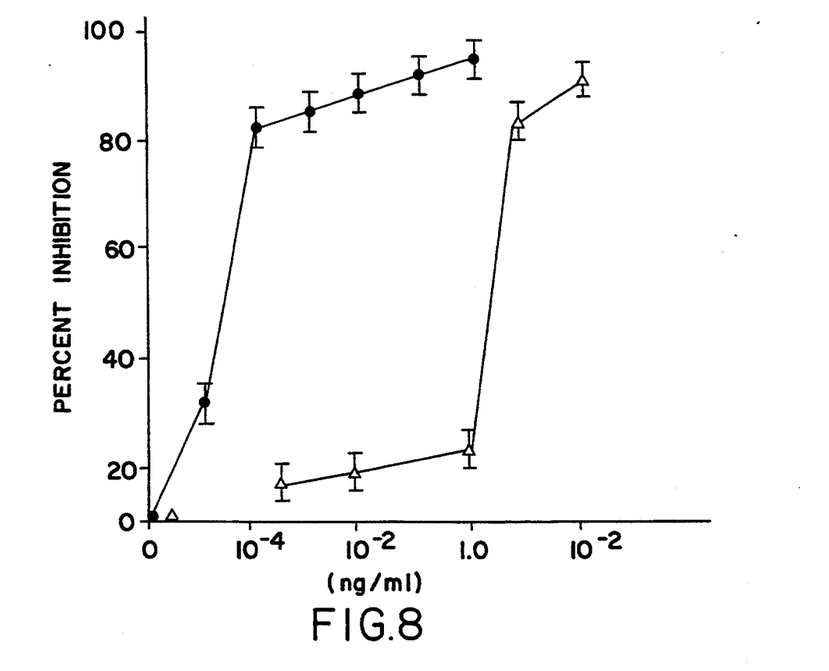
FIG. 8 graphically depicts the superior anti-malarial effects of IRDNA and IRDNB as compared to chloroquine in chloroquine-sensitive and chloroquine-resistant parasites.
Figure 9:
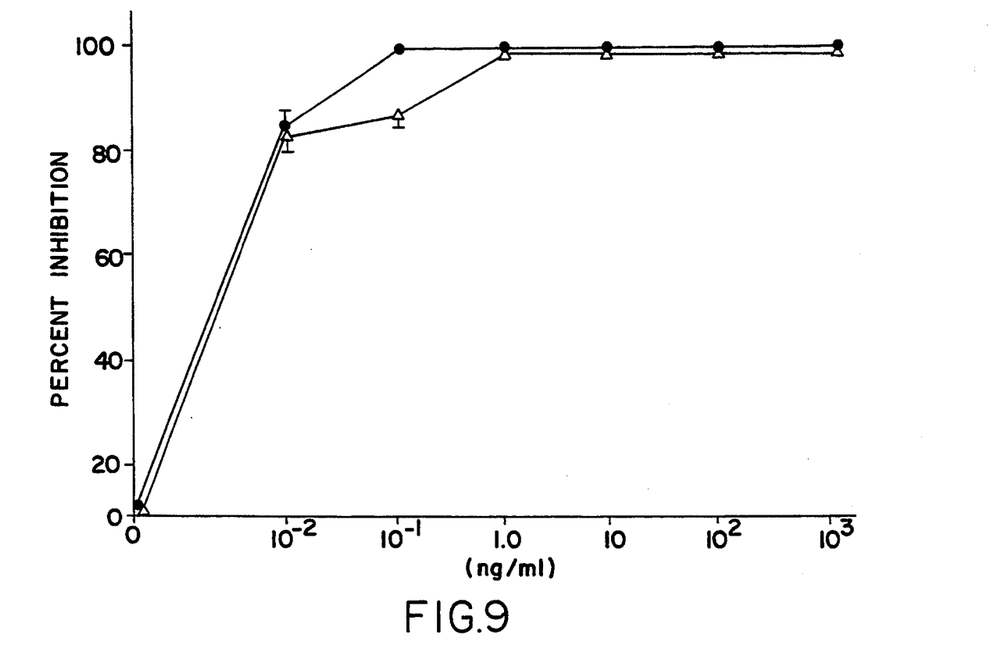
FIG. 9 graphically depicts the effectiveness of IRDNA in eliminating maturing gametocytes.
Figure 10:
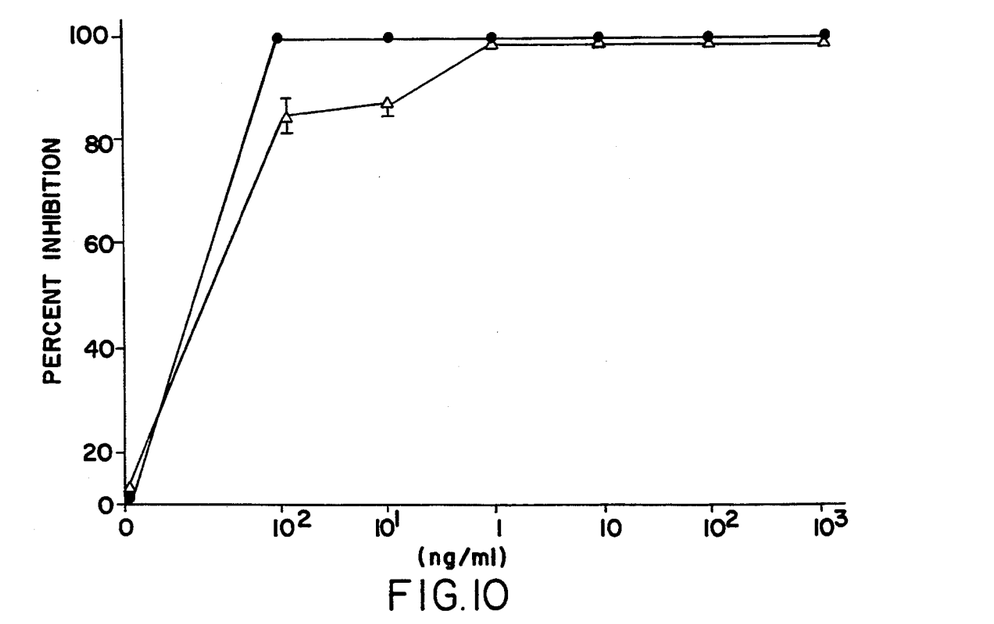
FIG. 10 graphically depicts the effectiveness of IRDNB in eliminating maturing gametocytes.

As shown in FIGS. 4–12, the Neem leaf extract products had inhibitory effects on sexual (gametocytes) as well as the asexual malarial parasites. Specifically, FIGS. 4–6 show that IRAB at a concentration of 5 $\mu$g/ml completely eliminates both sexual and asexual malarial parasites from cultures in 48 to 72 hours with an $ID_{50}$ of less than 1 $\mu$g/ml. FIG. 7 shows that IRDNA (closed circles) and IRDNB (squares) caused complete elimination of the sexual and asexual parasites at a very low dose of $10^{-2}$ ng/ml. The effect of chloroquine (triangles) is also shown. FIG. 8 shows that this inhibitory effect of IRDNA (closed circles) and IRDNB is the same for drug sensitive and resistant parasites, and better than the effect of chloroquine, (triangles), presently, the most used anti-malarial drug. The Neem leaf extracts were also equally effective in eliminating maturing gametocytes (FIGS. 9 and 10, at 48 hours (triangles) and 72 hours (closed circles) and previously mature gametocytes (FIGS. 11 and 12, at 48 hours (triangles) and 72 hours (closed circles). Thus, the in vitro activity of IRDNA and IRDNB when compared to the known anti-malarial drug chloroquine demonstrate that they should be effective in both treating malarial infection and preventing the spread of the infection to other individuals.

Cancerous Infection

Cancer is a broadly defined disease state which encompasses malignancy of various cells including for example the cells of the lymphatic system (lymphoma), blood cells (leukemia), breast, colon, brain, prostate and skin (melanoma). Many of these cancerous disease states such as monocytic leukemia, acute lymphoblastic leukemia and histiocytic lymphoma are characterized by metastasis. Thus, an anti-adhesive effect on the cancerous cells to prevent their colonization during metastasis would be beneficial to the treatment of these diseases.

Figure 13:
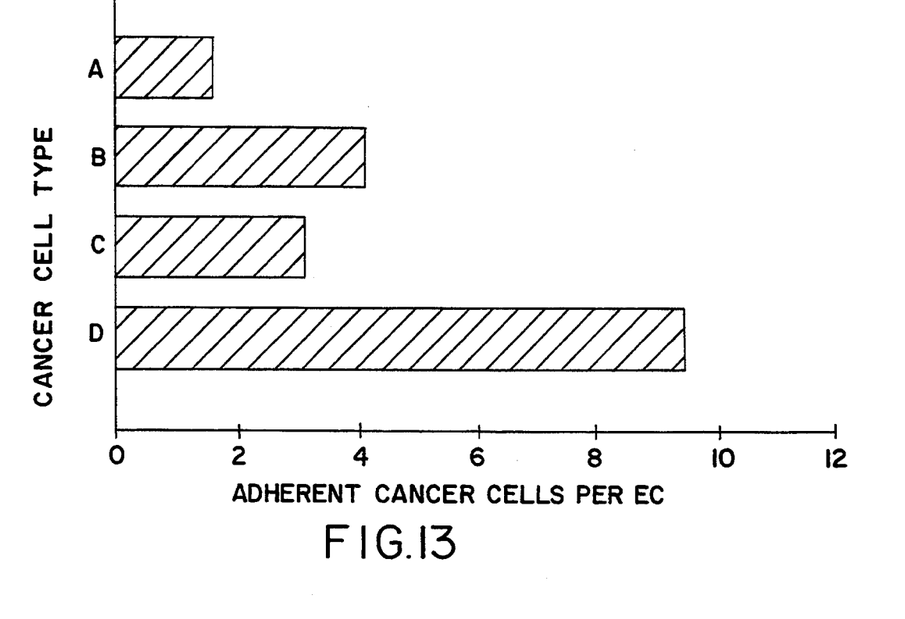
FIG. 13 graphically depicts the control for a cancer cell adhesion assay.
Figure 14:
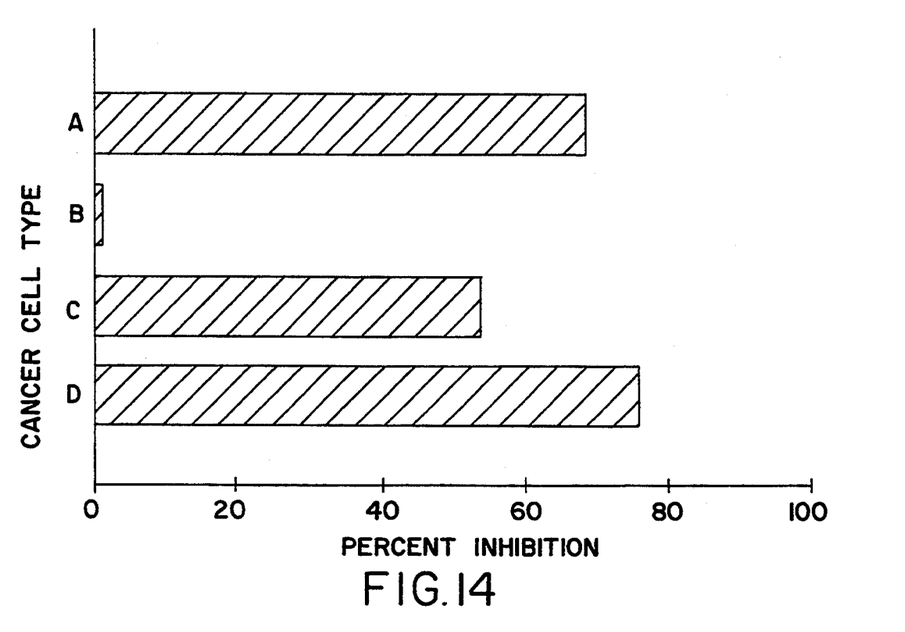
FIG. 14 graphically depicts the results of a cancer cell adhesion assay with Neem leaf extract IRAB.

Such an anti-adhesive effect by IRAB on cancer cells has been demonstrated in vitro. Specifically, the anti-adhesive effect of IRAB against human monocytes, histiocytes and lymphoblastic leukemia cells was assayed by the following procedure. Cancer cells of human monocytes (A;T1B202. THP-1), histiocytes (C; histiocytic lymphoma; CRL1593.U-937) and lymphoblastic leukemia cells, (C; histiocytic lymphoma; CRL1593.U-937) and normal human endothelial cells (EC-FP5 isolate), were separately cultured in a chamber filled with a gas mixture comprising oxygen 5%, carbon dioxide 5%, and nitrogen 90%. After 1–2 days of culture, some of the cancer cells were treated (incubated) with the extract IRAB at a concentration of 5.0 $\mu$g/ml for 15–30 minutes. Then, 1 ml of the treated cancer cells at $1 \times 10^6$ cells/ml was added to some of the endothelial cell cultures. Untreated cancer cells were added to other endothelial cells as control. The cells were then allowed to incubate for 60–90 minutes. After the incubation, nonadherent cancer cells were removed. The number of cancer cells adhered to the edothelial cells was determined by light microscopy at 1000x magnification. A decreased level of adhesion to the endothelial cells by the treated cancer cells compared to the control was indicative of antiadhesive activity of the tested Neem extract. A comparison of FIGS. 13 and 14 shows that IRAB has a significant anti-adhesive effect (i.e. 50–80%) against three of the four cancer cells tested. Thus, IRAB may be an effective compound for the treatment of some cancerous conditions.

Viral Infection

Vital infections are difficult to generally characterize because they frequently produce unapparent infections, and only occasionally overt disease. Nevertheless, due to their prevalence, they create important medical and public health problems. Some of the more commonly known viruses include HIV, yellow fever virus, sandfly fever (Sicilian) virus and the hepatitis viruses.

Figure 15:
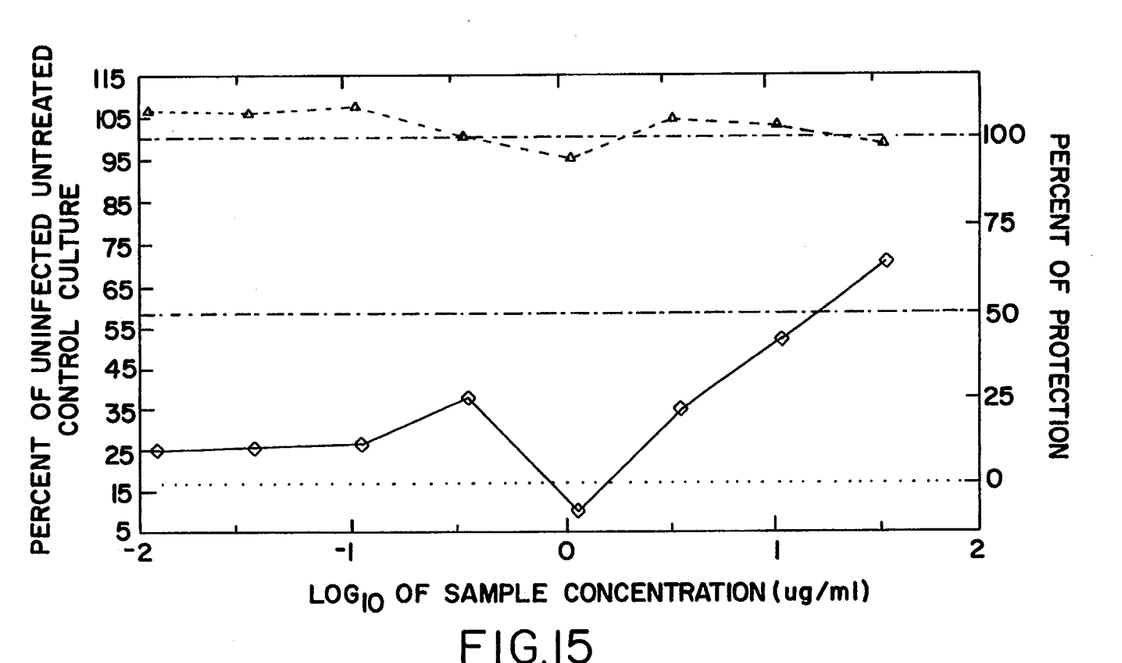
FIG. 15 graphically depicts the results of an in vitro anti-HIV assay with IRAB.

Assays to demonstrate inhibition of viral development are conducted by the following protocol. Vital target cell lines e.g. CEM-IW are grown in minimum essential medium (MEM) or medium 199 to monolayers in microtiter culture plates. To conduct the antiviral assay, the monolayers are infected with vital particles (in the present case the HIV), which are suspended in culture medium with, or without Neem extracts. After the infection period, 1–2 hours, the cells are washed with medium and incubated for 24 hours in 5% carbon dioxide at 37° C. The percentage of infected cells was determined by indirect immunofluorescence. A decrease in the percentage of infection in extract-treated cells compared to control indicates antiviral effect. In this assay, the Neem leaf extract product IRAB demonstrated an inhibitory effect on the development of HIV in vitro when used at a concentration of 10 $\mu$g/ml as shown in FIG. 15. The triangles represent the uninfected treated culture and the diamonds represent the infected treated culture.

Another assay to demonstrate anti-viral properties is the United States Army Medical Research Command (USAMRIID) Antiviral screen in which viral target cell line VERO monolayers were incubated with yellow fever virus or sandfly fever virus suspended in medium containing Neem leaf extracts. Cells incubated with viral suspensions without the Neem extracts were taken as controls. The cells were incubated for 1–2 hours for viral infection to occur. After which the cells were washed and cultured for 24 hours in 5% $CO_2$ at 37° C. The percentage of infected cells was determined by indirect immunofluorescence. Decrease in the percentage of infection in the Neem extract-treated cells compared to control was taken to indicate antiviral effect. In this assay, IRAB demonstrated activity against yellow fever virus and sandfly fever (Sicilian)

virus with $ID_{50}s$ of 119 μg/ml and 80.2 μg/ml, respectively. Thus, IRAB may be also an effective compound for the treatment of various viral infections.

Pharmaceutical Preparations

The compounds of this invention can be administered by oral, parenteral (intramuscular, intraperitoneal, intravenous (IV) or subcutaneous injection), nasal, vaginal, rectal, or sublingual routes of administration, and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs. These liquid dosage forms may contain inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals to obtain effective anti-malarial, anticancer or anti-viral activity.

The present invention is further illustrated by reference to the following examples. These examples are provided for illustrative purposes, and are in no way intended to limit the scope of the invention.

EXAMPLE 1

Extraction and Purification of Neem Leaf Products

Collection and Preparation of Leaves

Fresh green leaves were collected from mature trees. The leaves were oven dried at 40°–50° C. over several days to a crisp. The dried leaves were then ground to coarse powder using a waring blender and stored in plastic bags at room temperature until used.

Soxhlet Extraction of Leaves

For extraction, the ground leaves was weighed and loaded into 33 mm Whatman cellulose thimbles, 15–20 gm per thimble. After loading, the thimble was inserted into the soxhlet apparatus and solvent mixture 25-50 ml made up to 50/50 acetone and distilled water was poured into the thimble to soak the ground leaves overnight. The following day, the soaked ground leaves was subjected to standard soxhlet extraction using additional 100 ml of the solvent mixture stated above. Extraction temperature was set at 70°–85° C. The extraction lasted for 24 hours or until the color of the eluate (solution flowing into the reservoir flask from the thimble) became colorless from its initial or starting green color. The extraction process yielded a deep green cloudy liquid-extract which was stored in sealed glass jars overnight in a refrigerator at 0°–8° C.

Recovery of Extracted Compounds from Liquid Extract

Buchi-type rotor-evaporation system was used to recover both the solvent and extracted compounds from the liquid extract under vacuum at 80° C.–90° C.

Evaporation-Aided Separation Of Compounds IRC and IRAB

During the process of rotor-evaporation, fractions of the extracted compound continuously separated and precipitated on the sides of the rotor flask. As evaporation continued and after all the solvent were expelled, a brown oily liquid-residue remained. The oily liquid was poured out into a drying pan and dried to a paste overnight in air at 30°–40° C. The dried residue was recovered and code named IRC. To recover the precipitates on the sides of the rotor flask, 20–30 ml of acetone was poured into the flask and used to dissolve the precipitate. The solution was poured into a glass beaker and the acetone evaporated at room temperature over 1–2 days. The residue left after the evaporation of acetone was recovered and code named IRAB.

HPLC Fracionation of IRAB and Isolation of IRDNA and IRDNB

IRAB was weighed and dissolved in DMSO at 37° C. Stock solution was prepared to contain 100 mg/ml. For analysis, the stock solution was diluted to desired concentration (10–50 mg/ml) and then fractionated by analytical HPLC using the following parameters.

A prepacked 300 mm×7.8 mm I.D. 10 μM μ Bondapak $C_{18}$ preparative column (Waters Assoc.) was used to chromatograph all compounds isolated in this study. The stationary phase of μ Bondak $C_{18}$ is an octadecylsilyl bonded-phase packing material. The solid support medium contained in the column is capable of operating within a pH range of 2-8. It is thermally stable over a wide temperature range (<300° C.). Because of its excellent hydrolytic stability, various hydrophilic-hydrophobic mixed solvent systems are compatible with the column.

The mobile phase consisted of 0.02M glacial acetic acid mixed with acetonitrile. Two high pressure pumps were used to deliver the mobile phase. Acetonitrile-0.02M acetic acid at a 35:65 percent ratio was used in an isocratic mode. Flow-rate was 1.5 ml/minutes. Column pressures ranged between 72–80 bar. All separations were performed at ambient temperatures. Sample volumes were introduced into the column through a continuous flow loop injected. Fractionated aliquots containing the chromatographed peaks were collected during multiple injections of the crude extracts. Detection of each peak was accomplished using an ultraviolet detector, set at 254 nm. Peak areas were measured by an on-line computing integrator.

Under the stated fractionation conditions, IRDNA and IRDNB appeared as separate chromatographic peaks eluting at variable retention times (RT) of 25–28 minutes for IRDNA and 29–31 minutes for IRDNB. The amount of IRDNA and IRDNB eluted also varies in a typical fractionation, in which 4 mg of IRAB was fractionated, 0.6 mg and 0.9 mg of IRDNA and IRDNB, respectively were obtained, representing 15 and 22.5% respectively of the fractionated IRAB.

EXAMPLE 2

In Vitro Assay of Anti-adhesive Property Against *P. falciparum*-infected Erythrocytes Infected erythrocytes and human umbilical vein endothelial cells were separately cultured at 37° C. in a culture chamber filled with a gas mixture comprising oxygen 5%, carbon dioxide 5%, and nitrogen 90%. The malaria-infected erythrocytes were cultured in RPMI-1640 medium supplemented with 10% human serum, 3% sodium bicarbonate and HEPES buffer. The endothelial cells were cultured in medium 199 supplemented with 20% human AB serum, heparin 0.09 mg/ml, L-glutamine 2 mM, and endothelial cell mitogen 2 mgml. After 24 hours of culture, Neem leaf extracts from Example 1 were dissolved in dimethyl sulfoxide and added to the infected erythrocytes at concentrations of 5 $\mu$g/ml, 10 $\mu$g/ml, and 20 $\mu$g/ml. Then, 15–30 minutes following the addition of the extracts, the treated cells were added to endothelial cell cultures in 8 well culture plates at 1 ml of infected erythrocytes per well. The infected cell culture was at 2% hematocrit and 5% parasitemia. Untreated infected erythrocytes were added to other endothelial cell cultures as control. The cells were then incubated together for 90 minutes. After incubation, nonadherent infected erythrocytes were removed by aspiration. The number of the erythrocytes adhered to the endothelial cells were determined by light microscopy. A decreased level of adhesion to endothelial cells by treated infected erythrocytes as compared to control was used to indicate anti-adhesive effect of the tested Neem extract. This decreased level of adhesion is graphically depicted in FIG. 4 which shows that at a concentration of 5 $\mu$g/ml, IRAB completely inhibited adhesion of *E. falciparum*—infected erythrocytes to the human umbilical vein endothelial cells.

EXAMPLE 3

In Vitro Assay of Anti-Adhesive Property Against Cancer Cells

For this assay, human umbilical vein endothelial cells and cancer cells (monocytes, histiocytes, and lymphoblastic leukemia cells) were separately cultured in 5% carbon dioxide at 37° C. The cancer cells were obtained from the American Type Culture Collection (ATCC) in Rockville, Maryland. The endothelial cells were cultured in medium 199 supplemented with 20% human AB serum, heparin 0.09 mg/ml, L-glutamine 2 mM, and endothelial cell mitogen 2 $\mu$g/ml. The cells were cultured in 8 well culture plates until they reached 75% confluency. The cancer cells were maintained in Dolbeco's minimum essential medium supplemented with 5% fetal bovine serum.

For the anti-adhesive activity test, the Neem extracts from Example 1 were dissolved in dimethyl sulfoxide (DMSO) and added to the cancer cells at 5 $\mu$g/ml. After 15 minutes, the treated cancer cells were added with the extracts to endothelial cells. Untreated cancer cells as controls were also added to separate endothelial cells. The cells were incubated together for 90 minutes. After incubation, nonadherent cancer cells were aspirated off. The adhered cells were fixed with formalin and stained with Giemsa stain for microscopic observation. A descreased level of adhesion to the endothelial cells by treated cancer cells compared to control was indication of antiadhesive effect of the extract. This decreased level of adhesion was seen by comparing FIG. 14 (control) with FIG. 15. This comparison shows that IRAB has a significant anti-adhesive effect (i.e., 50–80%) against three of the four cancer cells tested; (human monocytes) T1B202.THP-1, human peripheral blood acute lymphoblastic leukemia CRL1552.MOLT-3, and human peripheral blood acute lymphoblastic leukemia CCL 119.CCRF-CEM).

EXAMPLE 4

In Vitro Assay of Inhibitory Effect of Neem Extract on Sexual and Asexual Malarial Parasites Human erythrocytes infected with the asexual 1TG2F6 isolate of *Plasmodium falciparum* were maintained in culture by established method which consists briefly, of culturing the infected cells at 37° C. in a gas mixture consisting of carbon dioxide 5%, oxygen 5%, and nitrogen 90% using medium RPM1-1640 supplemented with 10% serum, 3% sodium bicarbonate and HEPES buffer. For assays, the culture was adjusted to 2% hematocrit and parasitemia. The Neem extracts from Example 1 were dissolved in DMSO, and adjusted using culture media to obtain desired lower concentrations and to reduce the concentration of DMSO to non-toxic levels (<0.01%). The Neem extract solutions were then added to the malarial cultures. Different concentrations of the extract were used to treat the cultures (e.g. 0.05 to 5.0 $\mu$g/ml for IRAB; and $1 \times 10^{-4}$ to 10 ng/ml for IRDNA and IRDNB). Cultures of the infected erythrocytes without extract were used as control. Both control and treated cells were further cultured for 72 hours. Blood smears were made at intervals and at the end of the culture period and used to monitor the development of the malarial parasite, by light microscopy. Decrease in parasitemia in the treated cultures compared to control was observed, and indicated an anti-malarial effect of the extracts IRAB, IRDNA, IRDNB.

Details of the assay for inhibitory activity of Neem extracts on sexual malarial parasites is the same as for asexual forms except that the malarial isolate used in the assay was NF54 and the gametocytemia of the assay cultures varied between 0.1 to 1.0%. Also, the concentration of extracts used to treat the gametocytes varied between 0.05 to 5.0 μg/ml for IRAB and $1 \times 10^2$ to $1 \times 10^3$ ng/ml for IRDNA and IRDNB.

Figure 11:
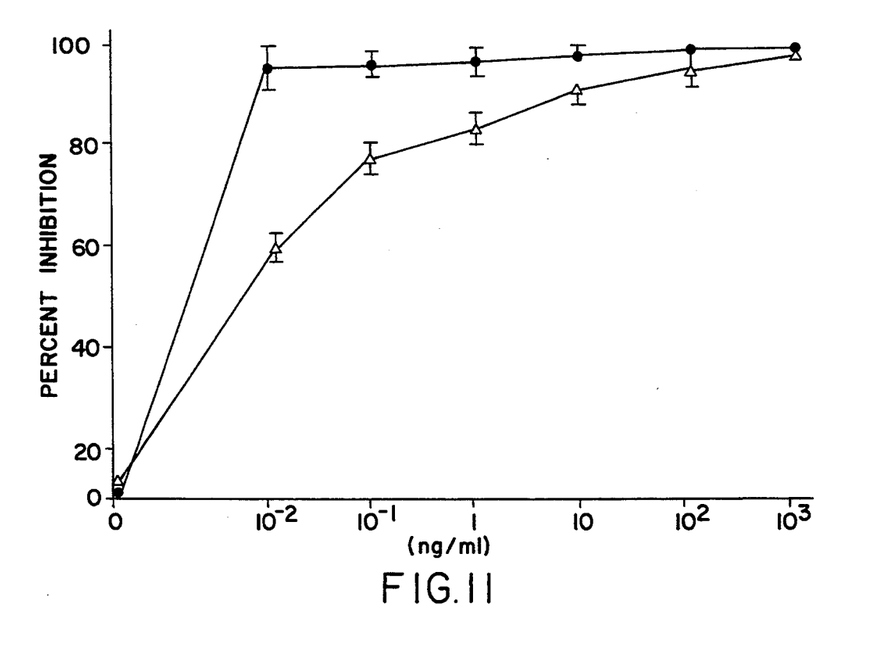
FIG. 11 graphically depicts the effectiveness of IRDNA in eliminating mature gametocytes.
Figure 12:
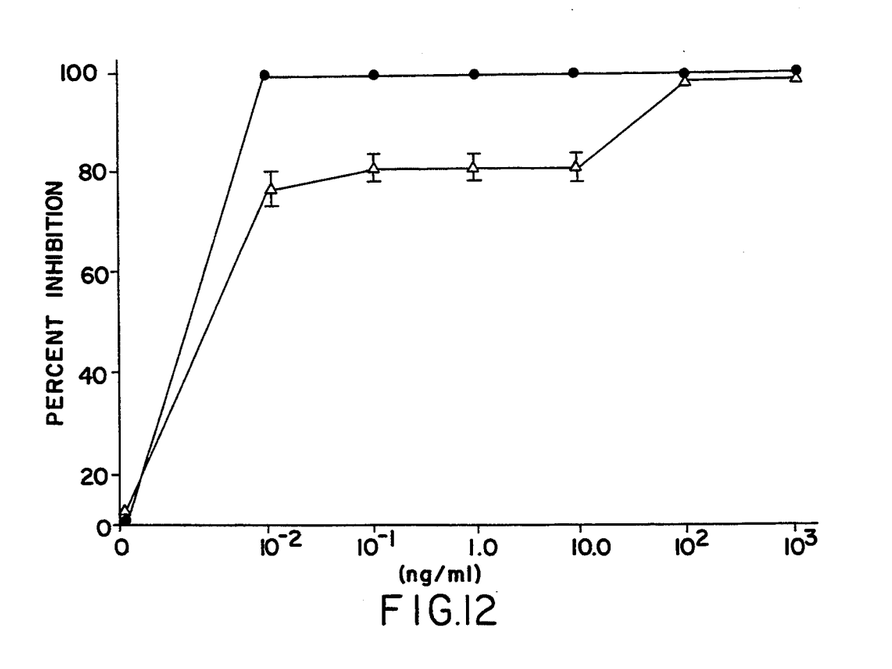
FIG. 12 graphically depicts the effectiveness of IRDNB in eliminating mature gametocytes.

As shown in FIGS. 4–6, IRAB at a concentration of 5 μg/ml completely eliminates both sexual and asexual malarial parasites from cultures in 48 to 72 hours with an $ID_{50}$ of less than 1 μg/ml. FIG. 7 shows that IRDNA and IRDNB caused complete elimination of the sexual and asexual parasites at a very low dose of $10^{-2}$ ng/ml. FIG. 8 shows that this inhibitory effect of IRDNA and IRDNB is the same for drug sensitive and resistant parasites, and better than the effect of chloroquine, presently, the most used anti-malarial drug. The Neem leaf extracts were also equally effective in eliminating maturing gametocytes (FIGS. 9 and 10) and previously mature gametocytes (FIGS. 11 and 12).

EXAMPLE 5

In Vitro ASSAY of Anti-Viral Properties

The in vitro antiviral assay was conducted as follows. For in vitro anti-HIV antiviral assay, the viral target cell line CEM-IW was cultured to monolayer in microliter culture plates. Culture medium was medium 199 supplemented with 10% inactivated fetal calf serum, penicillin (100 U/ml) and streptomycin (100 μg/ml). The cells were maintained in 5% carbon dioxide at 37° C. For the in vitro vital infection, the cells were placed in ice, and washed with ice-cold medium. Washed cells were then infected with vital particles suspended in cold medium at an M01 of 1.0 p.f. u/cell. After 1 hour, the cells were washed with warmed medium, and incubated for 24 hours in 5% $CO_2$ at 37° C. Infectivity was determined after 24 hours by indirect immunofluorescence.

For determination of antiviral effect of Neem extracts, the cells (CEM-IW) were incubated for 1 to 2 hours with viral particles suspended in medium containing the Neem extract IRAB. After the incubation with viral particles, the cells were washed with medium and further incubated for 24 hours as usual. Untreated viral particles were used as control. Decrease in the infectivity of the virus in the treated cells compared to control was observed, and indicated the antiviral activity of the Neem extract IRAB as shown in FIG. 15 and Table 3.

TABLE 3

In Vitro Anti-HIV Drug Screening Results

| Summary | | Dose | Infected Response | Uninfected Response |
|---|---|---|---|---|
| Index | Concent. | (ug/ml) | % Control | % Control |
| IC50* | $>3.60 \times 10^{+1}$ | $1.14 \times 10^{-2}$ | 25.26 | 106.39 |
| EC50* | $1.69 \times 10^{+1}$ | $3.61 \times 10^{-2}$ | 25.74 | 105.78 |
| TI50** | $>2.13 \times 10^{0}$ | $1.14 \times 10^{-1}$ | 26.58 | 107.45 |
| | | $3.61 \times 10^{-1}$ | 37.93 | 100.06 |
| | | $1.14 \times 10^{0}$ | 9.86 | 95.13 |
| | | $3.60 \times 10^{0}$ | 34.89 | 104.19 |
| | | $1.13 \times 10^{+1}$ | 51.79 | 102.52 |
| | | $3.60 \times 10^{+1}$ | 70.58 | 98.21 |

*μg/ml
**IC/EC

Anti-viral assay against other viruses namely sandfly fever virus, and yellow fever virus was the same as for HIV antiviral assay except that the target cell in the sandfly fever, and yellow fever virus antiviral assay was the VERO cell line instead of CEM-IW cell line.

While the invention has been described in connection with specific embodiments thereof, it is understood that the invention is capable of further modifications. Thus, this disclosure is intended in an illustrative rather than in a limiting sense, as it is contemplated that modifications will readily occur to those skilled in the art within the spirit of the invention and the scope of the appended claims.

What is claimed is:

1. An extract of Neem leaves which inhibits the adhesion of *Plasmodium falciparum* infected erythrocytes to cultured endothelial cells, said extract selected from the group consisting of an extract designated IRAB, a purified extract designated IRDNA and a purified extract designated IRDNB.

2. The extract of claim 1 designated IRAB.

3. The extract of claim 1 designated IRDNA.

4. The extract of claim 1 designated IRDNB.

5. A pharmaceutical preparation comprising a pharamceutically effective amount of the extract of claim 1 and a physiologically acceptable carrier.

6. A pharmaceutical preparation comprising a pharmaceutically effective amount of the extract of claim 2 and a physiologically acceptable carrier.

7. A pharmaceutical preparation comprising a pharmaceutically effective amount of the extract of claim 3 and a physiologically acceptable carrier.

8. A pharmaceutical preparation comprising a pharmaceutically effective amount of the extract of claim 4 and a physiologically acceptable carrier.

* * * * *